(12) United States Patent
Luigi

(10) Patent No.: US 6,733,556 B1
(45) Date of Patent: May 11, 2004

(54) ANTIBACTERIAL/ANTIVIRAL FILTERING DEVICE FOR VENTILATION SYSTEMS

(76) Inventor: Pier Luigi, Via Migliaro 4, I-16032 Camogli (IT)

(*) Notice: Subject to any disclaimer, the term of this patent is extended or adjusted under 35 U.S.C. 154(b) by 53 days.

(21) Appl. No.: 10/148,021

(22) PCT Filed: Nov. 15, 2000

(86) PCT No.: PCT/EP00/11281
§ 371 (c)(1),
(2), (4) Date: May 24, 2002

(87) PCT Pub. No.: WO01/37912
PCT Pub. Date: May 31, 2001

(30) Foreign Application Priority Data

Nov. 26, 1999 (IT) ......................... GE99A0138

(51) Int. Cl.[7] ........................... B01D 46/02; B01D 46/10
(52) U.S. Cl. ................ 55/385.1; 55/482; 55/482.1; 55/485; 55/503; 55/DIG. 32; 96/68; 96/294; 128/205.29
(58) Field of Search .................. 55/385.1, 482, 55/482.1, 485, 490.1, 503, DIG. 32, DIG. 35; 128/205.12, 205.27, 205.29, 205.28, 911; 96/294.4, 65, 66, 68

(56) References Cited

U.S. PATENT DOCUMENTS 4,360,918 A   11/1982   Ruhnau et al.

FOREIGN PATENT DOCUMENTS

| WO | WO 93/16749 | 9/1993 | |
| WO | WO 98/22172 | * 5/1998 | .......... A61M/16/00 |

* cited by examiner

Primary Examiner—Duane Smith
Assistant Examiner—Jason M. Greene
(74) Attorney, Agent, or Firm—Stites & Harbison PLLC; Douglas E. Jackson

(57) ABSTRACT

In a ventilation system, such as anaesthesia machines or ventilators for intensive care, provided with a hosed directed to patient, a breathable gas supplying tube, an exhaustion tube and an antibacterial/antiviral filtering device connected at one side to the hose and at the other side to the breathable gas supplying tube and to the exhaustion tube, the filtering device including a casing, provided with an inlet conduit connected to the breathable gas supplying tube, and an outlet conduit connected to the hose; the casing having at least two chambers having parallel axes, defined by at least a common wall, and in fluid connection one with the other.

8 Claims, 6 Drawing Sheets

US 6,733,556 B1

ANTIBACTERIAL/ANTIVIRAL FILTERING DEVICE FOR VENTILATION SYSTEMS

TECHNICAL FIELD OF THE INVENTION

The present invention relates to an antibacterial/antiviral filtering device for ventilation systems, such as anaesthesia machines or ventilators for intensive care.

BACKGROUND OF THE INVENTION

Patients receiving respirator care are often susceptible to infection during the ventilation. For this reason, it is important to filter the air coming from the respirator from foreign bacteria, viruses, or the like. Also, it is very important to prevent the contamination of the ventilation system; a valuable solution is described in U.S. Pat. No. 4,360,018.

Moreover, the air coming from the respirator is dry and has a relatively low temperature which would make the lungs dry up; should the air be not humidified before its introduction into the patient.

To achieve a solution for both the above problems, it has been proposed to provide a device in which the volume of the filter container is increased in order to achieve an adequate heat and moisture exchange capacity. For this reason, such a combination of heat/moisture exchanger and bacterial filter will be larger than in the case of a device comprising only a filter with the same filtering capacity. However, a larger volume increases the so called dead volume in the respiratory system of the patient. A larger dead volume in the respiratory system give rise to a greater degree of rebreathing of the patient's exhalation air, resulting in a larger content of carbon dioxide in the air inhaled.

In document WO-A-93/16749 a filter is described which is provided, in a relatively small volume, with a large exchange surface. However, even this solution does not eliminate a certain dead volume in the ventilation system.

In document WO 98/22172 a method for providing assisted ventilation which avoids hypoxia and hypocapnia is disclosed, in which a predetermined dead space in an assisted ventilation system is provided to the patient. The method may also be used to create normocapnia or moderate hypercapnia without causing hypoxia during assisted ventilation. The device has a proximal terminal and a coaxial filter device. According to the said prior art device separated flow circuits are provided for the air inspired and for the air expired by the patient.

SUMMARY OF THE INVENTION

The main object of the present invention is therefore to provide a filtering device in which the problem of the dead volume is completely eliminated, thus allowing a much more operational liability of the ventilation apparatus.

A further object of the invention is to provide a filtering device of the kind above defined, which is able to provide heat and moisture to the airflow directed to the patient's lungs.

A subject of the present invention is therefore an antibacterial/antiviral filtering device for ventilation systems, such as anesthesia machines or ventilators for intensive care, provided with a hose directed to patient. A breathable gas supplying tube, an exhaustion tube and an antibacterial/antiviral filtering device are connected at one side to the hose and at the other side to the breathable gas supplying tube and to the exhaustion tube. The filtering device also comprises a casing, provided with an inlet connected to the breathable gas supplying tube, and an outlet conduit connected to the hose. The filtering device is further characterized in that the casing comprises at least two chambers having parallel axes, which are defined by means of at least a common wall, and in fluid connection one with the other. A first chamber is in communication with the inlet conduit, and is provided with an antibacterial/antiviral filter. The second chamber is in communication with a conduit connected to the exhaustion tube, and with the conduit. The pressure of the inlet breathable gas is thus normally higher than that of the exhaled gas.

BRIEF DESCRIPTION OF THE DRAWINGS

Other advantages and features of the device according to the present invention will be more evident from the following detailed description of some preferred embodiments of the invention, shown in the appended drawings, in which.

DESCRIPTION OF SOME PREFERRED EMBODIMENTS OF THE INVENTION

Figure 1:
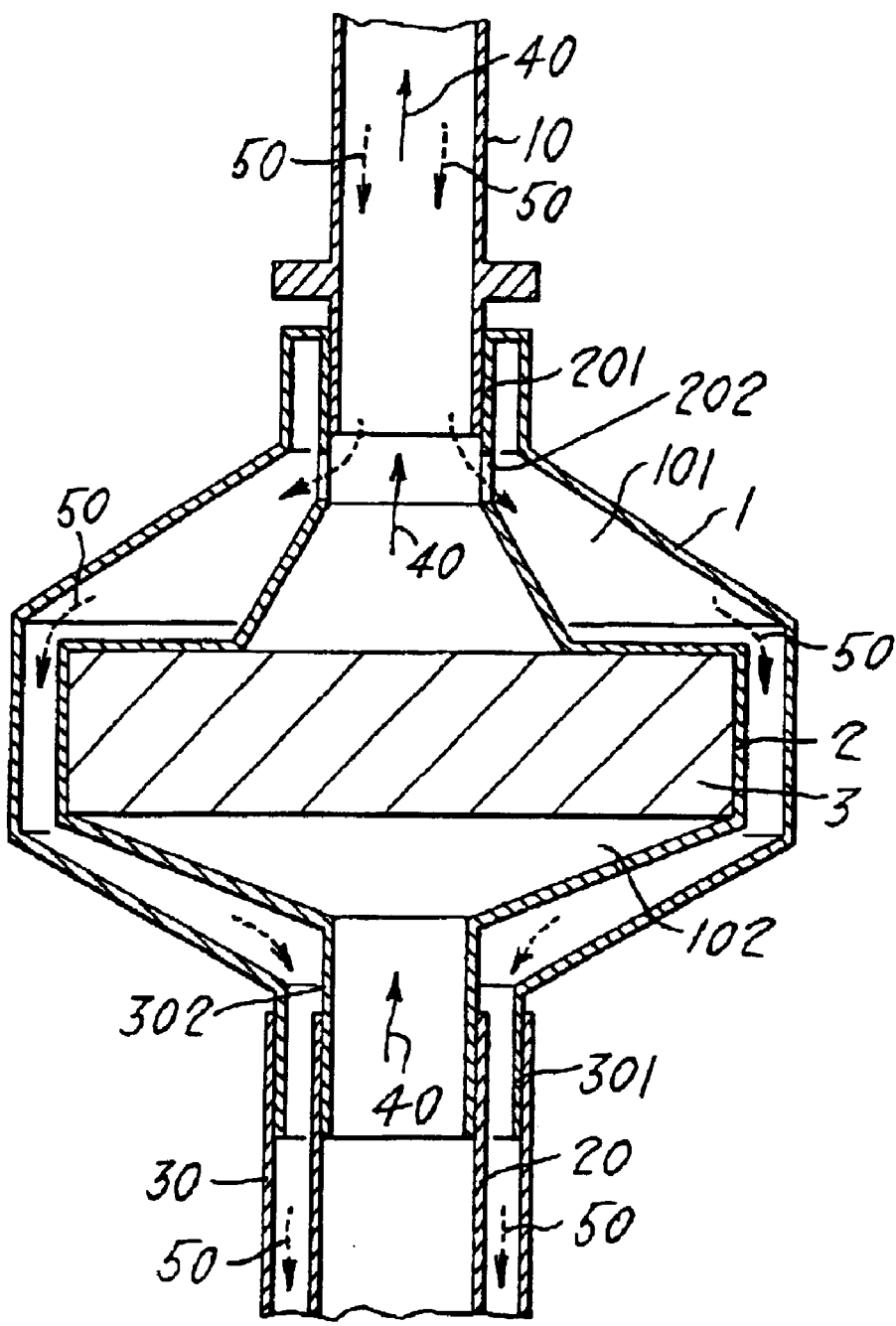
FIG. 1 is a longitudinal sectional view of a first embodiment of the present invention.

In FIG. 1 is illustrated a first embodiment of the filtering device according to the present invention. According to this embodiment, the device shown is connected at an end with a hose 10 directed to the patient and at the other end with a breathable gas supplying tube 20, connected to the ventilation apparatus, not shown, and to the exhaustion tube 30. The exhaustion tube 30 and the breathable gas supplying tube 20 are coaxial one with the other. The filtering device comprises an outer tubular casing 1, having a substantially circular cross-section; inside the said outer casing 1 an inner tubular wall 2, which is integral to the said outer casing 1, defines two chambers 101 and 102, which are coaxial one with the Other. The two chambers 101 and 102 communicates by means of two openings 202 formed into the wall 2. The openings 202 are formed in the wall 2 near the conduit 201, which is connected to the hose 10. In the innermost chamber 102 is placed an antibacterial filter 3, and the said chamber is provided with a conduit 302 connected to the breathable gas supplying tube 20. The outermost chamber 101 communicates with the exhaustion tube 30 by means of a conduit 301.

From the operating point of view, the breathable gas 40 flows into the chamber 102 via the supplying tube 20 and the conduit 302. Then, the gas expands in the chamber 102 and in the filter 3, and contacts the wall 2, which is in thermal exchange relationship with the chamber 101 surrounding it; subsequently, the gas flows in the hose 10, connected to the chamber 102 by means of the conduit 201. In the said chamber 101 flows the gas exhaled by the patient, having a temperature higher than that of the inlet gas 40: by this way, the breathable gas 40 inspired by the patient from the hose 10 is conveniently pre-heated. The exhaled gas 50 flows spontaneously into the chamber 101 from the openings 202, owing to the pressure of the inlet breathable gas 40 which is normally higher than that of the exhaled gas 50.

By this way the thermal exchanging surface is rather substantial, without any problem related to the dead volume. In fact, the separation of the exhaled gas 50 from the breathable gas 40 operated at the height of the openings 202, guarantees the substantial elimination of the said dead volume. The thermal exchange, which was formerly performed by mixing the two flows of gases, breathable gas and exhaled gas, is now possible, according to the present invention, only by contacting the wall 2 which separates the two chambers 101 and 102. The filter 3 is normally a filter performing a mechanical or electrostatic filtration.

Figure 2:
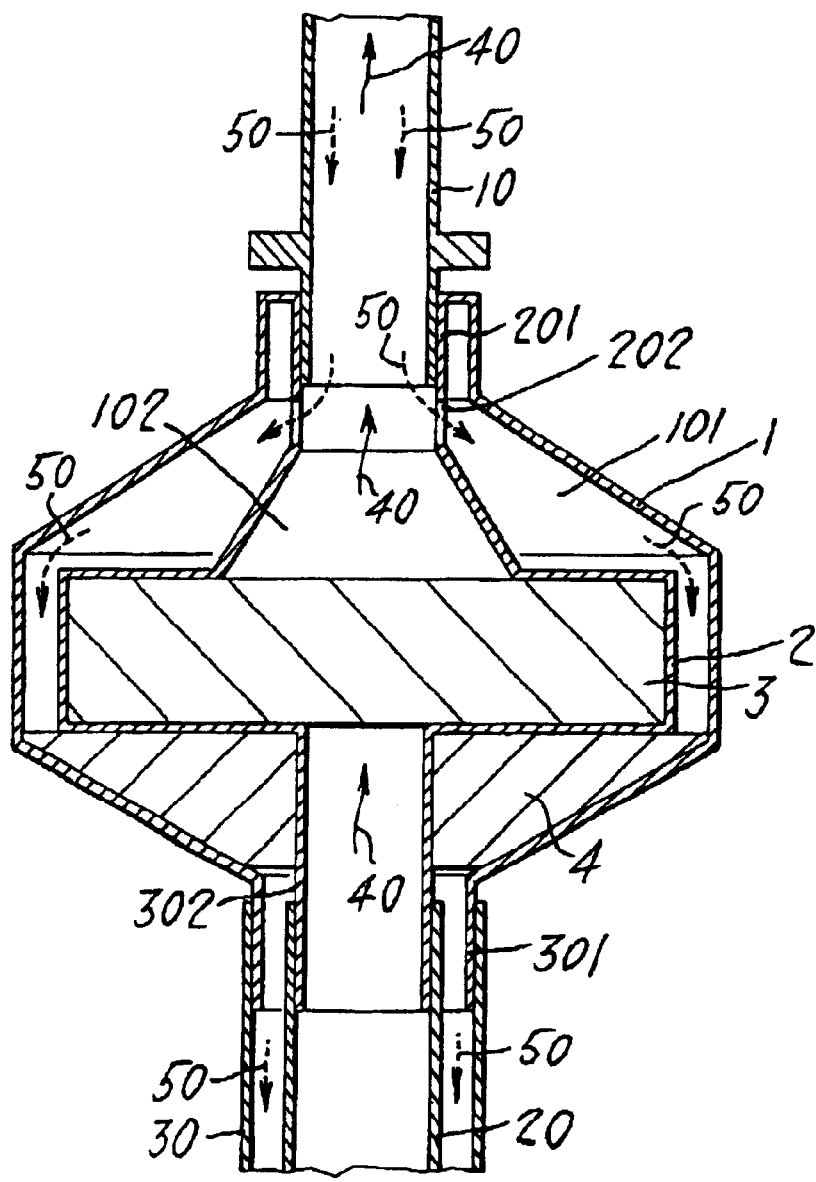
FIG. 2 is a longitudinal sectional view of a second embodiment of the present invention.

In FIG. 2 is illustrated a second embodiment of the present invention. The filtering device here shown is almost similar to that illustrated in FIG. 1 and above described, the same parts keeping the same numeral reference. The main difference relates to a further filter 4 placed into the chamber 101, which acts on the exhaled air flow coming from the patient.

This additional filter 4 is used in order to eliminate any possible infecting agent coming from the patient, thus preventing any pollution of the ventilation system. Also this filter 4, similarly to the above described filter 3, performs its filtering action mechanically or electrostatically.

Figure 3:
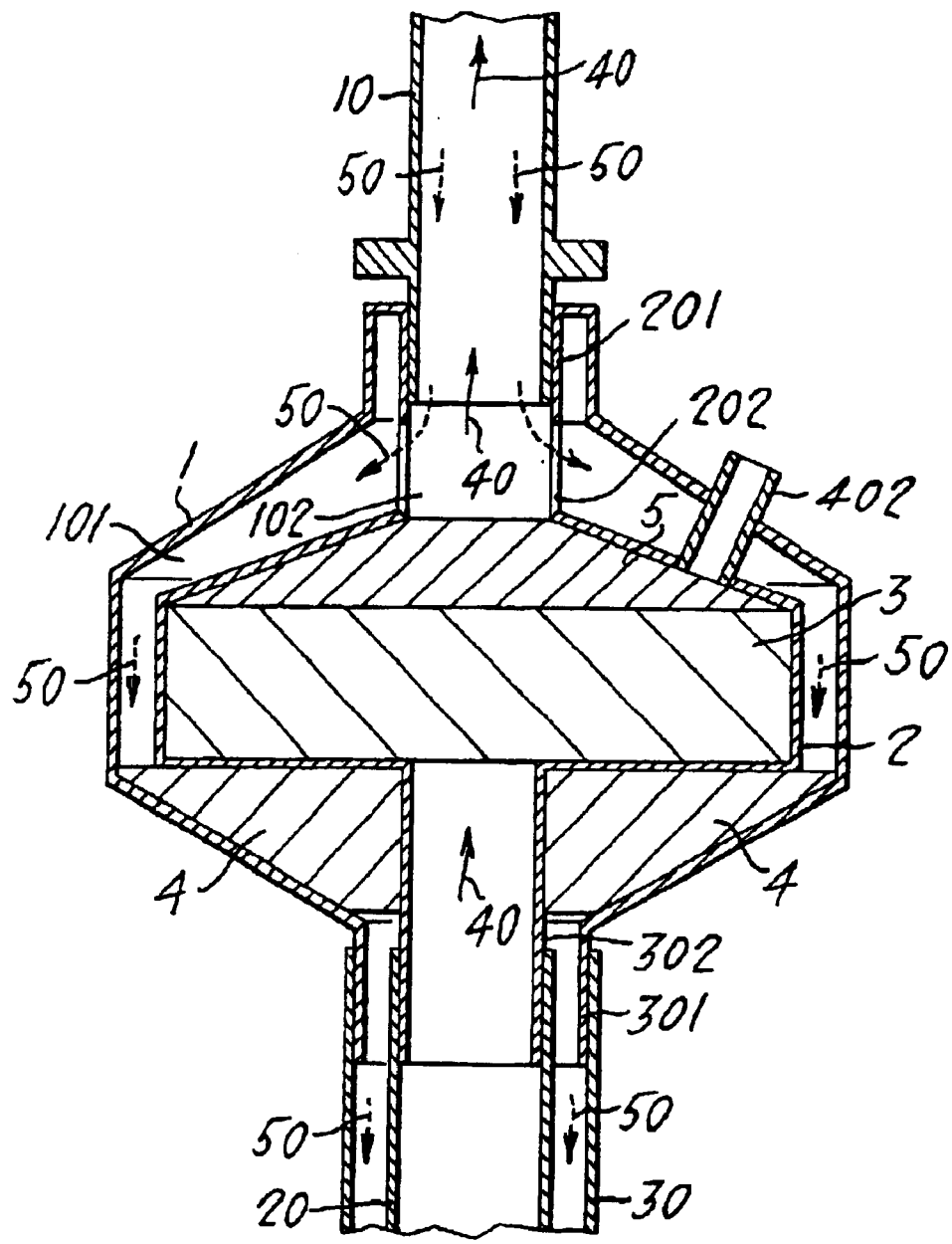
FIG. 3 is a longitudinal sectional view of a third embodiment of the present invention.

In the FIG. 3 is illustrated another embodiment of the present invention; the only difference between this filtering device and the filtering device above described is in that the filtering device is further provided with a humidifying filter 5, which is placed in a portion of chamber 102 located near the conduit 201 connected to the hose 10. The wall 2 of the chamber 102 is provided with a duct 402 for the supply of water to the said humidifying filter 5.

Figure 4:
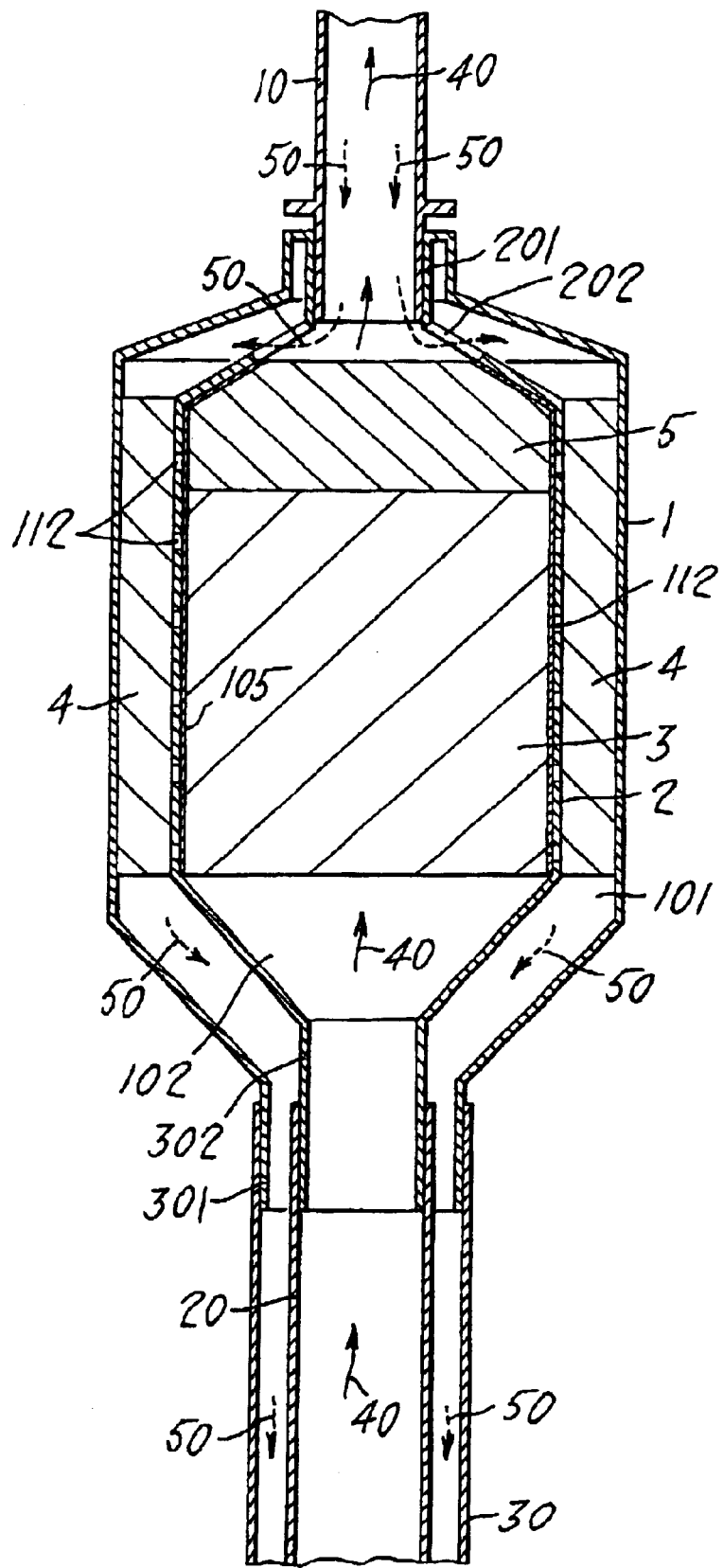
FIG. 4 is a longitudinal sectional view of a fourth embodiment of the present invention.

In the embodiment of FIG. 4, the chamber 102 and the filter 3 have relative greater dimensions in respect to those of the filtering devices above described. This increased dimension can allow a much more effective filtering capability of the filtering device. Moreover, several through holes 112 are formed into the wall 2, and the filters 3 and 5 are both encapsulated into the membrane 105. The said membrane 105 is an hydrophilic membrane, impermeable to the gases, so as to allow the recovery of the moisture present in the exhaustion gas flow 50.

Figure 5:
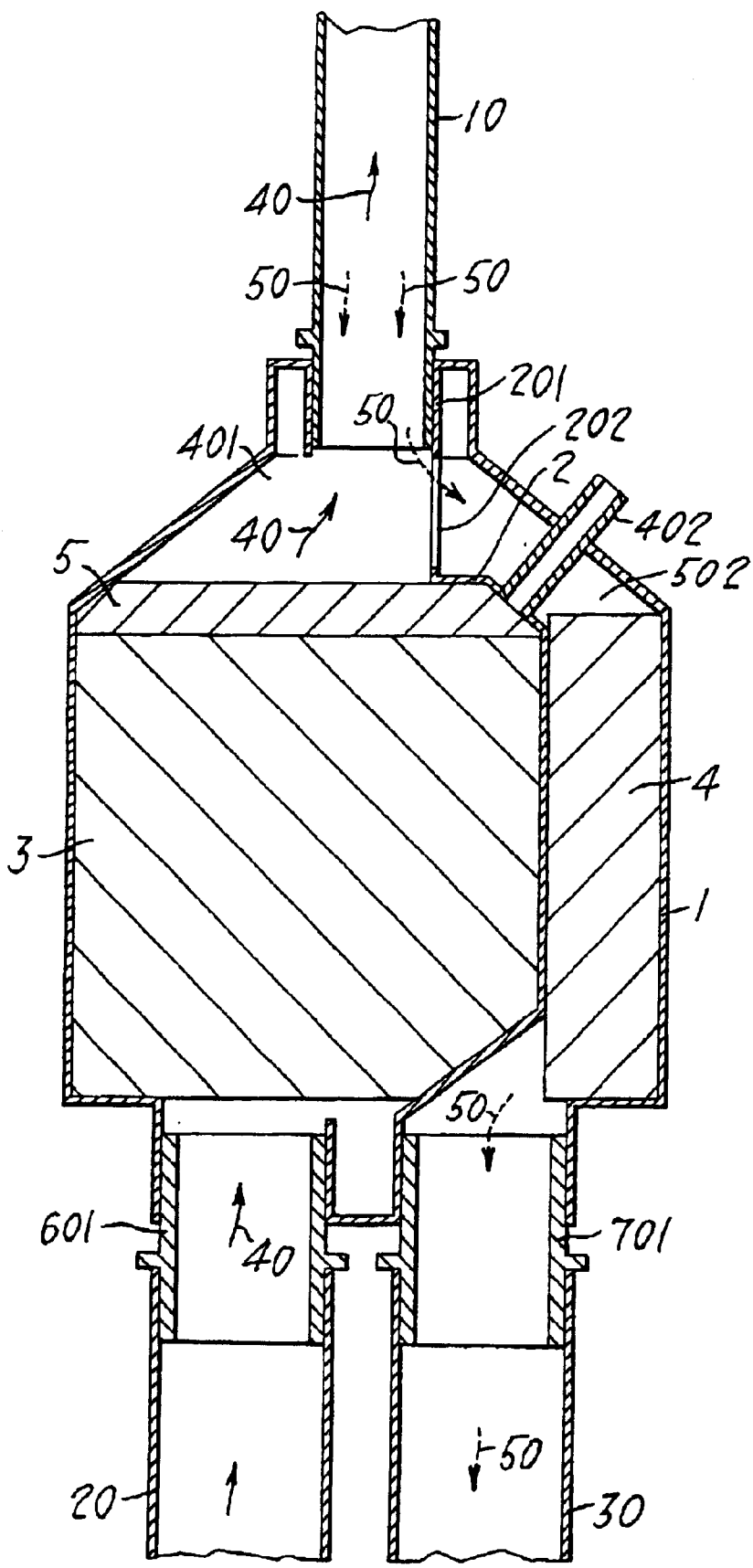
FIG. 5 is a longitudinal sectional view of a fifth embodiment of the present invention.

In FIG. 5 is described another embodiment of the present invention; in this filtering device the box-like outer casing 1 is divided into two chambers 401 and 502 having parallel axis, by the inner wall 2, which is integral to the said casing 1; the two chambers 401 and 502 communicate by means of the opening 202, formed through the wall 2 near the conduit 201 connected to the hose 10. The chamber 401 is connected to the breathable gas supplying tube 20 by means of the conduit 601. Inside the said chamber 401 is provided the antibacterial filter 3 and the humidifying filter 5, which is fed by means of the water supplying duct 402 formed on the wall 2. The chamber 502, provided with the filter 4, communicates with the exhaustion tube 30 by means of the conduit 701.

In this embodiment, the two chambers are not realized coaxial one with the other, but nevertheless the results achieved by the filtering device can be considered quite the same.

Figure 6:
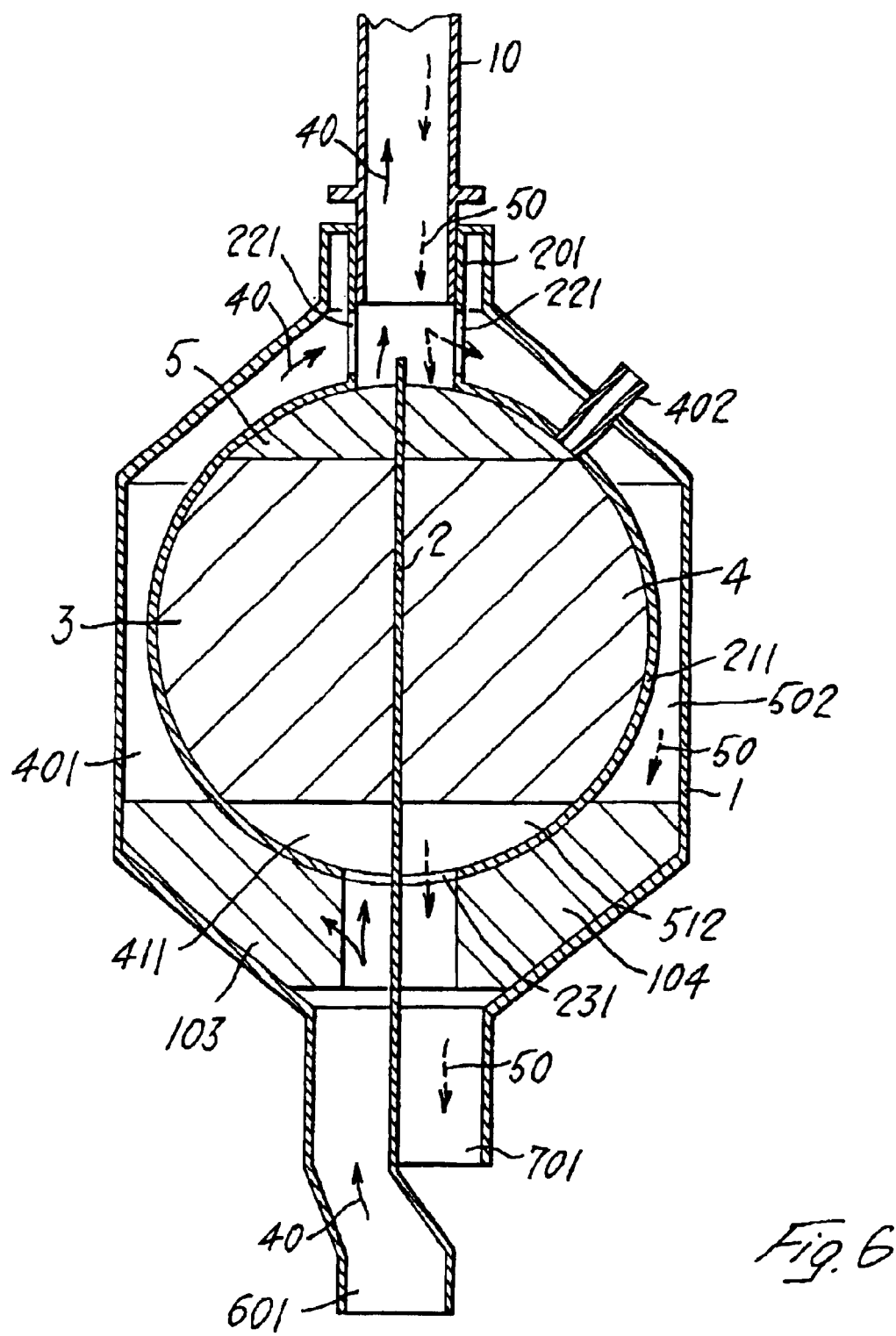
FIG. 6 is a longitudinal sectional view of a sixth embodiment of the present invention.

In the embodiment illustrated in FIG. 6, the casing 1 is also divided, as in the previously described embodiment, in two chambers 401 and 502 by a wall 2. Moreover, a substantially spherical wall 211 is provided, which is integral to the conduit 201 and which further gives rise to the inner chambers 411 e 512. In the said inner chambers 411 and 512 are located the filters 3 and 4, respectively. In the outer chambers 401 and 502 are located the filters 103 and 104, respectively.

This arrangement, very similar to that above described, further allows the use of two different kind of filter on both the inlet breathable gas flow and the exhaustion gas flow. For example, the filters 3,4 placed in the chambers 411 and 512 can be mechanical filters, and the filters 103 and 104 can be electrostatic filters.

A filtering device according to the present invention achieves, by the way above explained, a number of substantial advantages, such as:

elimination of the dead volume of the filter;

reduction of the total dead volume of the entire ventilation system;

elimination of the limitation upon the dimension of the filter, thus enhancing the effectiveness of the filtration;

elimination of the resistance of the filter in the exhaustion phase.

Possibility of the extension of the use of the filtering device also for the newborn

What is claimed is:

1. Antibacterial/antiviral filtering device for ventilation systems, provided with a hose directed to the patient, a breathable gas supplying tube, an exhaustion tube and an antibacterial/antiviral filtering device connected at one side to said breathable gas supplying tube and to said exhaustion tube, the said filtering device comprising a casing, provided with an inlet conduit connected to the breathable gas supplying tube, and an outlet conduit connected to the said hose, at least two chambers having a common wall; a first chamber being in communication with the inlet conduit of the breathable gas, and provided with an antibacterial/antiviral filter; the second chamber being in communication with a conduit connected to the exhaustion tube characterized in that the said two chambers have parallel axis, least a common wall and in fluid connection one with the other by means of one or more openings formed through said wall; that the said first chamber is in communication with the said inlet conduit of the breathable gas, and with the said outlet conduit; that the said second chamber is in communication with a conduit connected to the said exhaustion tube, and with the said outlet conduit, the pressure of the inlet breathable gas being higher than that of the exhaled gas.

2. Antibacterial/antiviral filtering device according to claim 1, wherein the second chamber is provided with an antibacterial/antiviral filter.

3. Antibacterial/antiviral filtering device according to claim 1, wherein the first chamber is provided with a humidifying filter, which is placed in a portion of chamber located near the said conduit.

4. Antibacterial/antiviral filtering device according to claim 3, in which the said wall is provided with a duct for the supply of water to the said humidifying filter.

5. Antibacterial/antiviral filtering device according to claim 3, in which said wall is provided with several through holes, the humidifying filter and the antibacterial/antiviral filter located in the said first chamber being encapsulated in a hydrophilic membrane, impermeable to the gases.

6. Antibacterial/antiviral filtering device according to claim 1, in which the said first chamber and the said second chamber are coaxial one with the other, the first chamber being the innermost one.

7. Antibacterial/antiviral filtering device according to claim 1, in which the said inlet conduit of the breathable gas and the said conduit for the exhaustion of the gas exhaled by the patient are coaxial one with the other, the inlet conduit being the innermost one.

8. Antibacterial/antiviral filtering device according to claim 1, in which the said filter provided in the said first chamber is a mechanical filter or an electrostatic filter.

* * * * *

UNITED STATES PATENT AND TRADEMARK OFFICE
CERTIFICATE OF CORRECTION

| | |
|---|---|
| PATENT NO. | : 6,733,556 B1 |
| APPLICATION NO. | : 10/148021 |
| DATED | : May 11, 2004 |
| INVENTOR(S) | : Delvigo |

It is certified that error appears in the above-identified patent and that said Letters Patent is hereby corrected as shown below:

Title Page, Item (76) should read:

(76) Inventor: Pier Luigi Delvigo, Via Migliaro 4, I-16032 Camogli (IT)

Title Page, Item (12) under United States Patent, Delete "Luigi" and insert,
-- Delvigo --.

Signed and Sealed this

Twenty-fourth Day of April, 2007

JON W. DUDAS
*Director of the United States Patent and Trademark Office*